(12) United States Patent
Ogura et al.

(10) Patent No.: US 9,322,934 B2
(45) Date of Patent: Apr. 26, 2016

(54) ELECTRONIC CASSETTE

(71) Applicant: FUJIFILM Corporation, Tokyo (JP)

(72) Inventors: Ryosuke Ogura, Ashigarakami-gun (JP); Shinsuke Noguchi, Ashigarakami-gun (JP); Takeyasu Kobayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 161 days.

(21) Appl. No.: 14/204,596

(22) Filed: Mar. 11, 2014

(65) Prior Publication Data

US 2014/0270092 A1   Sep. 18, 2014

(30) Foreign Application Priority Data

Mar. 12, 2013  (JP) ................. 2013-049296

(51) Int. Cl.
  *G03B 42/04* (2006.01)
  *G03B 42/02* (2006.01)
  *G01T 1/20* (2006.01)
  *A61B 6/00* (2006.01)

(52) U.S. Cl.
  CPC ............. *G01T 1/2006* (2013.01); *A61B 6/4233* (2013.01); *A61B 6/4283* (2013.01); *G03B 42/04* (2013.01)

(58) Field of Classification Search
  CPC ...... G03B 42/04; G03B 42/02; G03B 42/023; G03B 42/045; A61B 6/4283; A61B 6/4405; A61B 6/44; G01T 1/244
  USPC ........... 378/189, 167, 182, 62, 169, 174, 177, 378/180, 187; 250/370.09, 582, 239, 580
  See application file for complete search history.

(56) References Cited

U.S. PATENT DOCUMENTS

| 4,247,778 | A | | 1/1981 | Waerve | |
|---|---|---|---|---|---|
| 5,519,229 | A | * | 5/1996 | Verbeke | G03B 42/04 250/484.4 |
| 5,773,839 | A | * | 6/1998 | Krepel | G03G 15/758 250/370.09 |
| 7,459,714 | B2 | * | 12/2008 | Fukui | A61B 6/4283 250/581 |

(Continued)

FOREIGN PATENT DOCUMENTS

| JP | 2002-082172 A | 3/2002 |
|---|---|---|
| JP | 2010-217498 A | 9/2010 |

OTHER PUBLICATIONS

Extended European Search Report, dated Jun. 11, 2014, for European Application No. 14157855.9.

*Primary Examiner* — David A Vanore
(74) *Attorney, Agent, or Firm* — Birch, Stewart, Kolasch & Birch, LLP

(57) ABSTRACT

A chamfered portion configured to have a surface which is tilted to a side surface and a rear surface is formed between the side surface and the rear surface of a housing of an electronic cassette. The chamfered portion has a boundary portion having a predetermined range in the vicinity of a boundary including the boundary with the side surface; a boundary portion having a predetermined range in the vicinity of a boundary including the boundary with the rear surface, and the other portion which does not belong to these boundary portions. The chamfered portion needs to be smoothly inserted into a gap between a patient and an installation surface on which the patient lies on one's back. Therefore, an entire surface of these boundary portions is formed in a curved surface which protrudes outward from the housing.

11 Claims, 10 Drawing Sheets

(56) References Cited

U.S. PATENT DOCUMENTS

| | | | | |
|---|---|---|---|---|
| 7,909,510 B2 * | 3/2011 | Ohta | A61B 6/585 378/167 |
| 8,492,717 B2 * | 7/2013 | Ogura | A61B 6/4283 250/336.1 |
| 8,748,836 B2 * | 6/2014 | Sato | A61B 6/4283 250/370.09 |
| 8,901,505 B2 * | 12/2014 | Kobayashi | G01T 1/2018 250/369 |
| 8,942,346 B2 * | 1/2015 | Nicholson | A61B 6/06 378/147 |
| 8,981,309 B2 * | 3/2015 | Noguchi | G01T 1/20 250/370.01 |
| 9,006,671 B2 * | 4/2015 | Noguchi | G03B 42/04 250/370.04 |
| 2007/0297573 A1 * | 12/2007 | Fukui | A61B 6/4283 378/174 |
| 2009/0323900 A1 * | 12/2009 | Ohta | A61B 6/585 378/167 |
| 2010/0111263 A1 * | 5/2010 | Lamberty | A61B 6/4283 378/189 |
| 2010/0183123 A1 * | 7/2010 | Thiery | G03C 3/00 378/187 |
| 2011/0053289 A1 * | 3/2011 | Lowe | B01L 3/5027 436/501 |
| 2011/0248173 A1 * | 10/2011 | Ogura | A61B 6/4283 250/361 R |
| 2013/0043400 A1 * | 2/2013 | Nakatsugawa | A61B 6/4283 250/366 |
| 2013/0083900 A1 * | 4/2013 | Kobayashi | G01T 1/2018 378/189 |
| 2014/0270092 A1 * | 9/2014 | Ogura | G01T 1/2006 378/189 |
| 2015/0276944 A1 * | 10/2015 | Enomoto | G01T 1/161 378/101 |

* cited by examiner

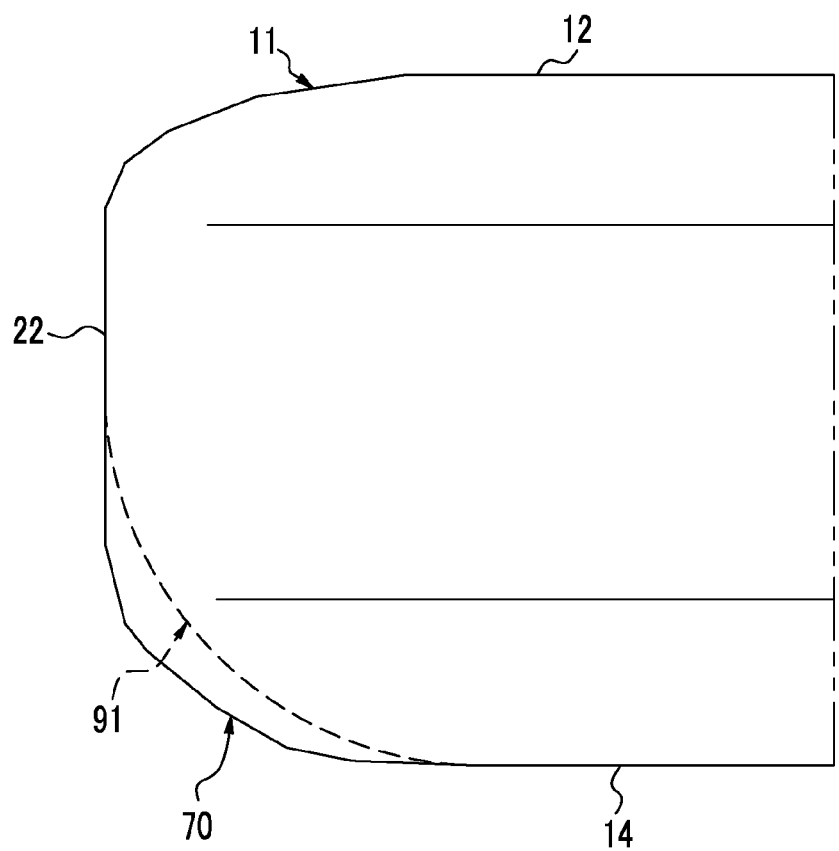

ELECTRONIC CASSETTE

BACKGROUND OF THE INVENTION

1. Field of the Invention

The present invention relates to an electronic cassette for use in radiography.

2. Description of the Related Art

An electronic cassette has been widely used in medical radiography, for example, in X-ray photography. The electronic cassette is a portable X-ray image detector which has a built-in image detection unit (flat panel detector (FPD)) for detecting an X-ray image of a photographic subject (such as a patient) inside a portable housing having a flat and rectangular parallelepiped shape.

The electronic cassette is used not only by being set on a dedicated photographing stand holder, but also by being attached to an existing photographing stand holder for a film cassette, an IP cassette and a CR cassette. Furthermore, in order to photograph a site which is unlikely to be photographed by using a stationary type which has an built-in X-ray image detector unremovable from the photographing stand, a user places the electronic cassette on a bed, or causes the electronic cassette to be held by a patient's own hand. In addition, in order to photograph an aged person in convalescence at home or emergency patients due to accidents, disasters or the like, in some cases, the electronic cassette is used outside hospitals which do not have facilities for the photographing stand. Since the electronic cassette is also used without being attached to the photographing stand holder, enhanced mobility and installation flexibility are required. In addition, since there is a possibility that the electronic cassette may directly come into contact with the patients, it is also important that the electronic cassette does not give discomfort to the patients when in contact.

JP2002-082172A discloses an electronic cassette that has a rectangular parallelepiped housing in which a chamfered portion formed from a plane tilted to a side surface and a rear surface is disposed between the side surface and the rear surface of the housing. The housing has a shape as if a corner at an intersection of the side surface and the rear surface is cut off in a planar shape. The chamfered portion is a tilted plane and the rear surface is also the plane. Accordingly, a boundary between the chamfered portion and the rear surface has an angle, although the angle is an obtuse angle. For example, when the electronic cassette is placed on a flat surface (hereinafter, referred to as an installation surface) in a state where the rear surface faces downward, a finger is allowed to enter a gap between the chamfered portion and the installation surface by disposing the chamfered portion described above. Accordingly, the finger is easily hooked on an end portion of the housing and thus it is easy to lift the electronic cassette up. In addition, since the chamfered portion is disposed between the side surface and the rear surface, as compared to the housing having a corner of 90° at the intersection of the side surface and the rear surface, the patient's contact feeling becomes softer when the end portion of the housing comes into contact with the patients.

SUMMARY OF THE INVENTION

As described above, in some cases, the electronic cassette is used for a patient who lies on one's back on a bed, an aged person or an emergency patient who cannot move by oneself. In this case, first, in a posture where the electronic cassette is tilted so that one side surface of the housing faces downward, the end portion of the housing is inserted into a gap between the patient and the installation surface on which the patient lies on one's back. Then, while the patient is lifted up, the housing is further deeply pushed into the gap. In this manner, the electronic cassette is set to be located at a desired photographing position.

The electronic cassette disclosed in JP2002-082172A has a chamfered portion in the end portion of the housing, but the boundary between the chamfered portion and the rear surface has a corner. This corner causes a resistance by being caught on the installation surface when the end portion of the housing is inserted into the gap between the patient and the installation surface on which the patient lies on one's back. For this reason, the electronic cassette disclosed in JP2002-082172A has a problem in that the end portion of the housing is unlikely to be inserted into the gap between the patient and the installation surface on which the patient lies on one's back.

The present invention is made in view of the above-described problem, and an object thereof is to provide an electronic cassette which can be smoothly inserted into a gap between a patient and an installation surface on which the patient lies on one's back.

In order to achieve the above-described object, the present invention provides an electronic cassette including an image detection unit that detects a radiographic image of a photographic subject; a rectangular parallelepiped housing that accommodates the image detection unit, and that has a front surface on which radiation is incident, a rear surface opposing the front surface, and four side surfaces; and a chamfered portion that is disposed between at least one of the side surfaces and the rear surface, and that is configured to have a surface tilted to the side surface and the rear surface. A boundary portion between the chamfered portion and the rear surface is formed in a curved surface which protrudes outward from the housing.

An entire surface of the chamfered portion which includes a boundary portion with the rear surface and a boundary portion with the side surface is formed in a curved surface which protrudes outward from the housing.

The chamfered portion satisfies a condition of $h<d1$ when assuming that a height of the housing in a thickness direction is h and a length in a horizontal direction which is orthogonal to the thickness direction is d1 in the respective boundaries between the rear surface and the side surface. More specifically, the height h is 7 mm to 10 mm and the length d1 is 20 mm to 40 mm.

In a cross-sectional shape of the chamfered portion, the boundary portion with the rear surface is an arc or an elliptical arc which is formed by cutting off a portion from a perfect circle or an ellipse. In this case, the rear surface is a tangent to the perfect circle or the ellipse, and the boundary between the chamfered portion and the rear surface is a tangent point to the perfect circle or the ellipse.

It is preferable that the largest member out of members accommodated inside the housing satisfy a condition of $d2<d3$ when assuming that the shortest distance between an end portion of the largest member whose planar size is largest and an inner wall surface of the side surface is d2 and the shortest distance between the end portion of the largest member and an inner wall surface of the chamfered portion is d3. For example, the largest member is a base to which a circuit board is attached. In addition, it is preferable that when the largest member is arranged in the thickness direction inside the housing, the largest member be fitted within a range of a height from the boundary between the chamfered portion and the side surface to the front surface.

It is preferable that the rear surface have a battery mounting unit on which a battery unit for supplying power to the image detection unit is detachably mounted and which is a concave portion in which the rear surface is recessed toward the front surface, and that when the battery mounting unit is arranged in the thickness direction inside the housing, the battery mounting unit be fitted within a range of a height from the rear surface to the boundary between the chamfered portion and the side surface.

According to the present invention, a boundary portion which is a portion including at least a boundary with a rear surface of a housing has a chamfered portion formed in a curved surface which protrudes outward from the housing. Therefore, it is possible to smoothly insert the electronic cassette into a gap between a patient and an installation surface on which the patient lies on one's back.

BRIEF DESCRIPTION OF THE DRAWINGS

FIG. 10 is a view for comparing chamfered portions in which heights of housings are the same as each other and the height h of one chamfered portion is equal to the length d1.

FIG. 11A is an overall view, and FIG. 11B is an enlarged view of an insertion point, respectively.

FIG. 12A illustrates an arc-shaped chamfered portion, and FIG. 12B illustrates an elliptical arc-shaped chamfered portion.

DESCRIPTION OF THE PREFERRED EMBODIMENTS

Figure 1:
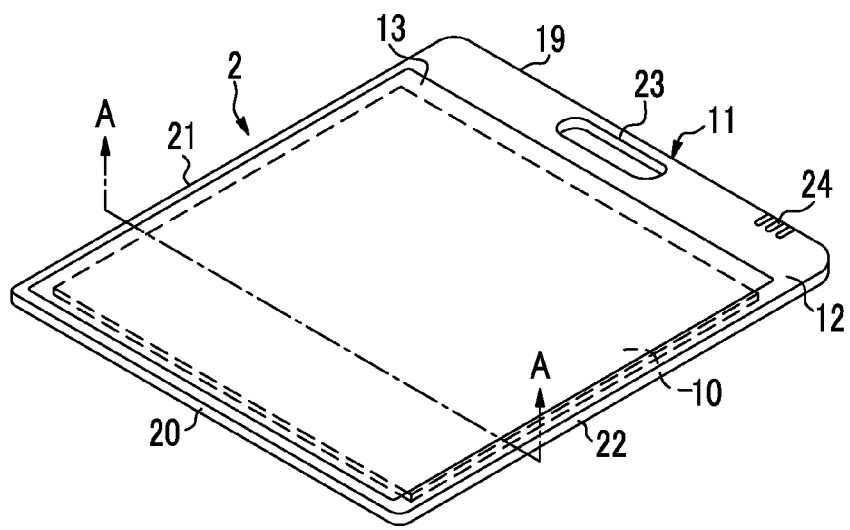
FIG. 1 is a perspective external view of an electronic cassette when viewed from a front surface side.
Figure 2:
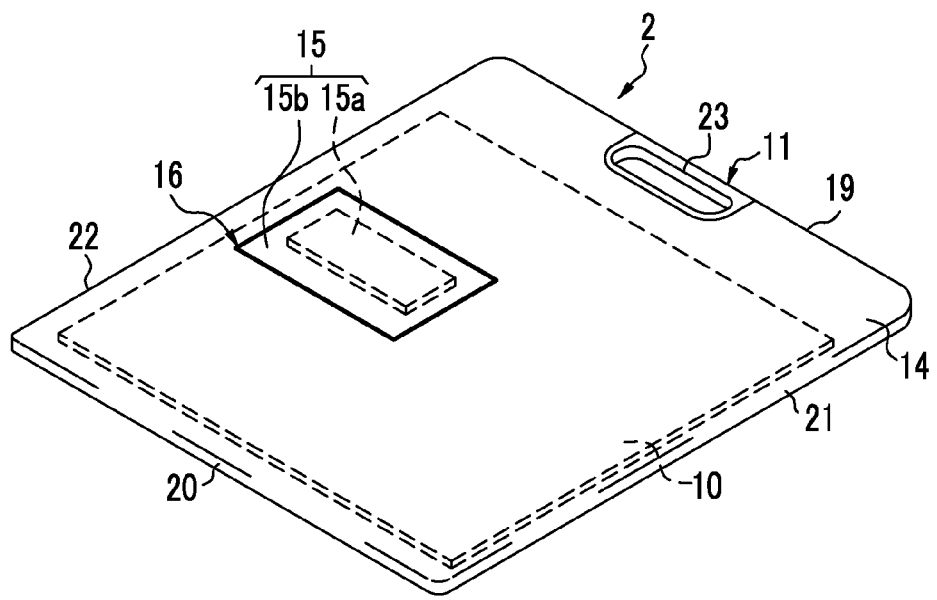
FIG. 2 is a perspective external view of an electronic cassette when viewed from a rear surface side.

In FIGS. 1 and 2, an electronic cassette 2 is configured to have an image detection unit 10 and a portable housing 11 which accommodates the image detection unit 10. For example, the housing 11 is formed of a conductive resin. As illustrated in FIG. 1, a rectangular opening is formed on a front surface 12 of the housing 11 on which an X-ray is incident, and a transmission plate 13 serving as a top plate is attached to the opening. The transmission plate 13 is formed of a carbon material which is lightweight, highly rigid and extremely permeable to the X-ray.

In FIG. 2, a battery unit 15 which supplies power for driving the image detection unit 10 is mounted on a rear surface 14 of the housing 11 which opposes the front surface 12. The battery unit 15 is configured to have a battery 15a and a box-shaped battery case 15b which accommodates the battery 15a. A battery mounting unit 16 on which the battery unit 15 is detachably mounted is disposed on the rear surface 14. FIG. 2 illustrates a state where the battery unit 15 is mounted on the battery mounting unit 16 and the battery unit 15 is locked by a locking mechanism (not illustrated) so as not to fall out from the battery mounting unit 16. A connector 17 (refer to FIG. 3) is disposed in the battery unit 15 and a socket 18 (also refer to FIG. 3) is disposed in the battery mounting unit 16, respectively. When the battery unit 15 is mounted on the battery mounting unit 16, the connector 17 and the socket 18 are fitted and electrically connected to each other.

Figure 4:
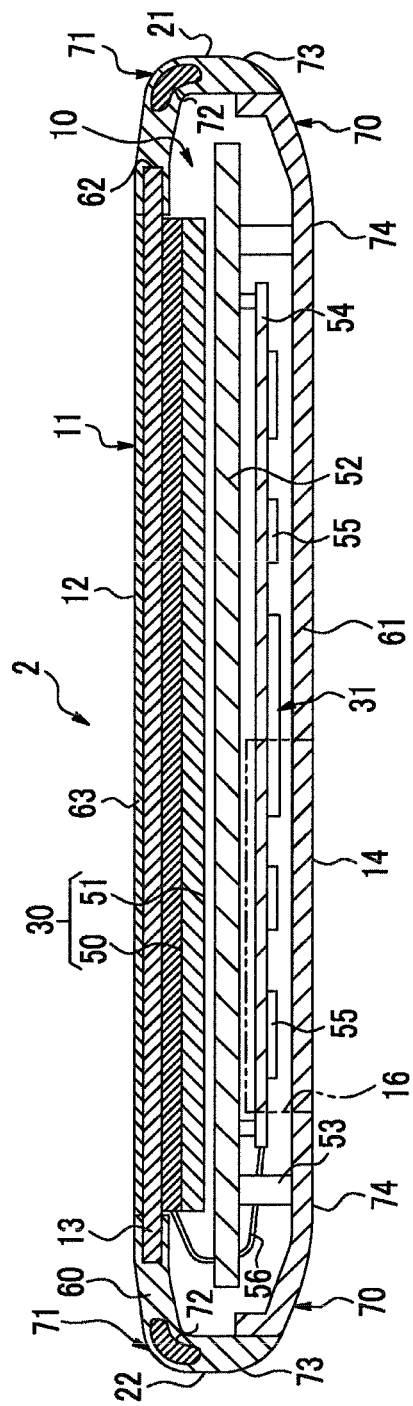
FIG. 4 is a cross-sectional view of an electronic cassette taken along line A-A in FIG. 1.
Figure 5:
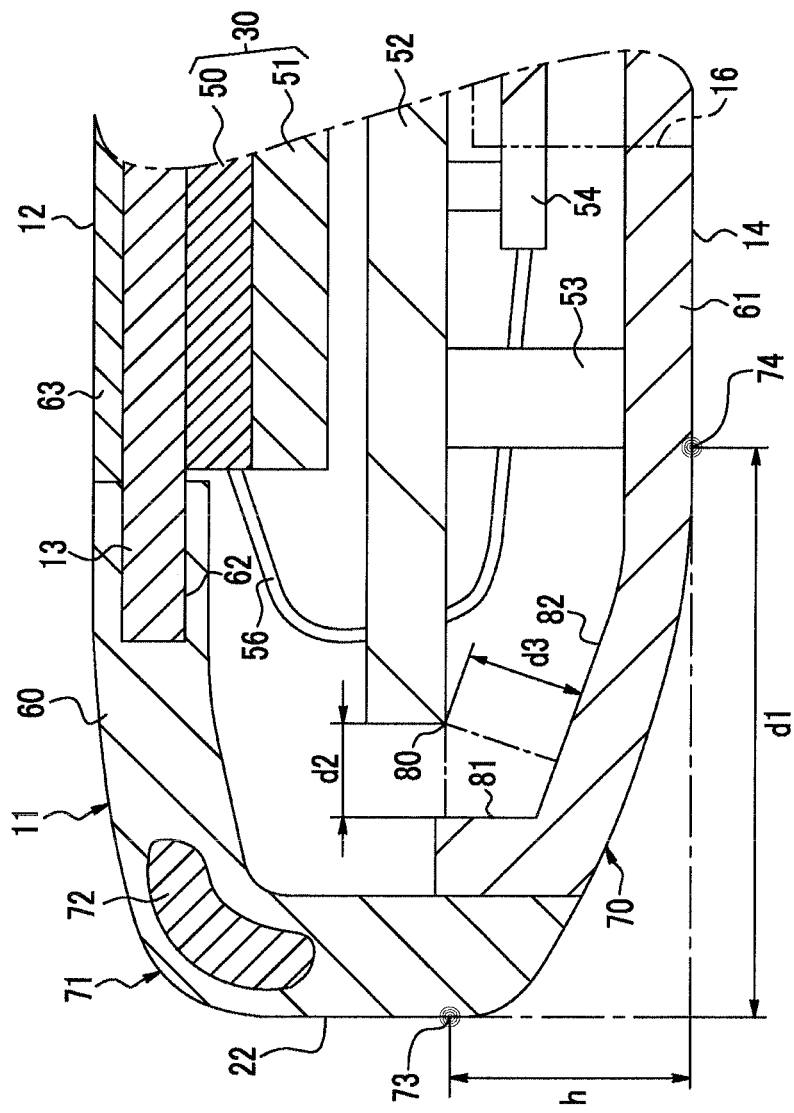
FIG. 5 is an enlarged cross-sectional view in the vicinity of a chamfered portion.

The battery mounting unit 16 is a concave portion in which the rear surface 14 is recessed toward the front surface 12 (refer to FIGS. 4 and 5). The battery mounting unit 16 is formed in the same shape and the same size as the planar shape and the planar size of the battery unit 15 so that the battery unit 15 is fitted thereto substantially without gap. The depth from the rear surface 14 of the battery mounting unit 16 is also substantially the same as the thickness of the battery unit 15. Therefore, when the battery unit 15 is mounted on the battery mounting unit 16, the upper surface of the battery unit 15 is exposed from the rear surface 14 and the upper surface of the battery unit 15 and the rear surface 14 are on the same plane. In FIGS. 4 and 5, the inner wall surface of the battery mounting unit 16 is illustrated by a two-dot chain line.

The housing 11 has a rectangular parallelepiped shape configured to have the front surface 12, the rear surface 14 and four side surfaces 19, 20, 21 and 22. The housing 11 has a size compliant with the international standard ISO4090: 2001 substantially the same as a film cassette, an IP cassette and a CR cassette. The electronic cassette 2 is set to be attachable to and detachable from a holder of an upright photographing stand or a decubitus photographing stand so that the electronic cassette 2 is held in a posture where an X-ray source for irradiating X-rays and the front surface 12 oppose each other. In addition to that the electronic cassette 2 is set on the upright photographing stand or the decubitus photographing stand, the electronic cassette 2 is sometimes used alone for a patient who cannot move on one's own, such as a patient who lies on one's back on a bed, an aged person or an emergency patient. Furthermore, since the electronic cassette 2 has substantially the same size as that of the film cassette, the IP cassette and the CR cassette, the electronic cassette 2 can be attached to the existing photographing stand for these cassettes. The electronic cassette 2 may not have the size which is compliant with the international standard ISO4090: 2001.

A handle 23 through which an operator's hand passes through when the operator carries the electronic cassette 2 is formed on an upper side portion of the side surface 19 side of the housing 11. In addition, an indicator 24 such as an LED is disposed to indicate power on/off of the electronic cassette 2 or a remaining amount of the battery unit 15. The housing 11 also functions as an electromagnetic shield to prevent intrusion of electromagnetic noises on the electronic cassette 2 and outward radiation of the electromagnetic noises from the electronic cassette 2.

Figure 3:
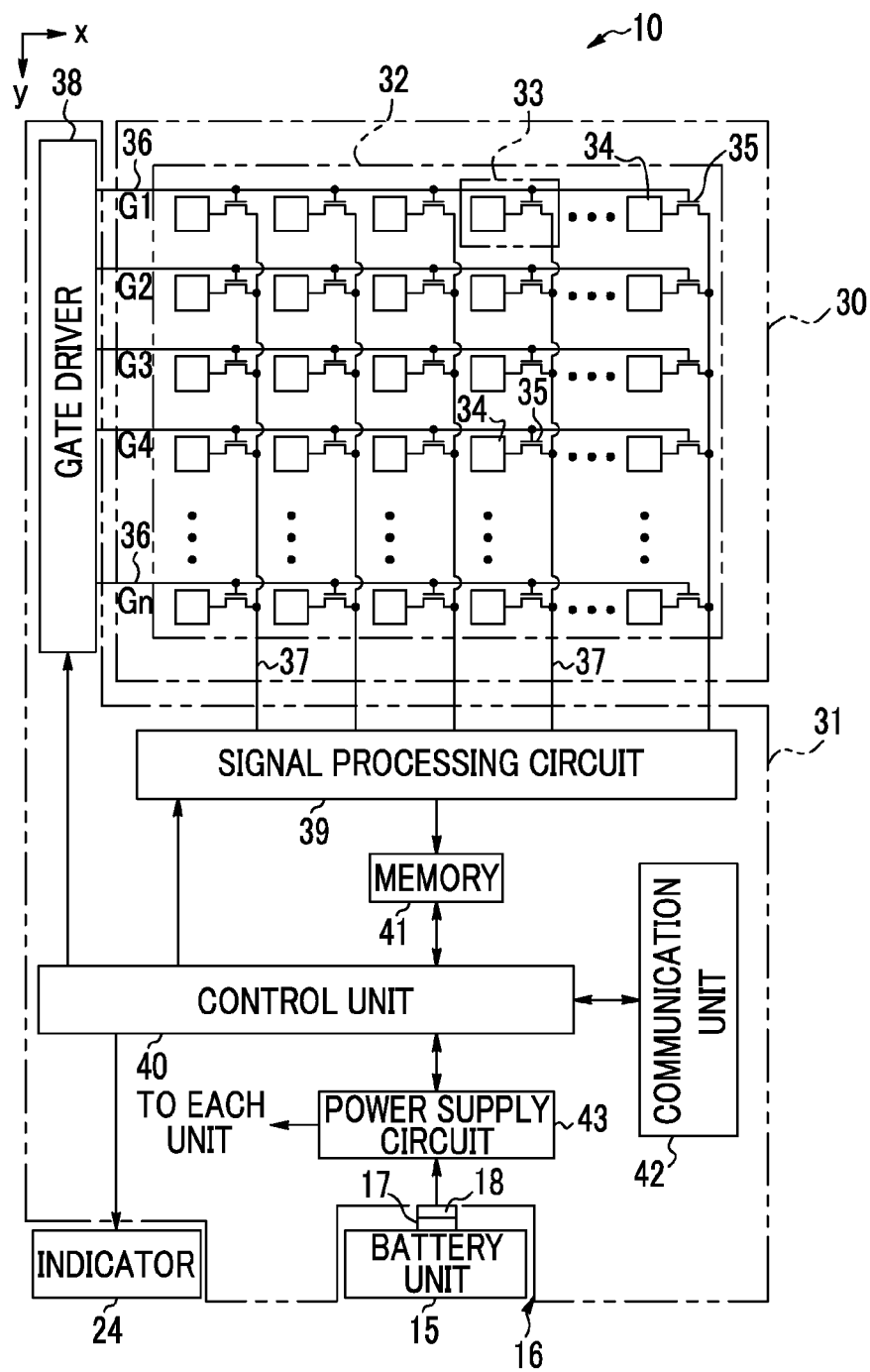
FIG. 3 is a block diagram illustrating an internal configuration of an electronic cassette.

In FIG. 3, the image detection unit 10 has a panel portion 30 and a circuit portion 31. The panel portion 30 has a thin film transistor (TFT) active matrix substrate 50 made of glass (refer to FIGS. 4 and 5, hereinafter, simply referred to as a TFT substrate). An imaging region 32 is formed in the TFT substrate 50. In the imaging region 32, multiple pixels 33 for accumulating charge corresponding to an irradiation dose of X-rays are arranged at a predetermined pitch in a matrix of n rows (x-direction)×m columns (y-direction). The n or m is an integer of two or more. For example, n or m≅2,000. Array of the pixels 33 may not be square array as in the present embodiment, and may be honeycomb array.

The panel portion 30 has a scintillator 51 (phosphor, refer to FIGS. 4 and 5) which converts X-rays into visible light beams, and is an indirect conversion type which photoelectrically converts on the visible light beams converted by the scintillator 51 into the pixels 33. The scintillator 51 is configured to have CsI: Tl (thallium-activated cesium iodide) or GOS (Gd2O2S: Tb, terbium-activated gadolinium oxysulfide), and is arranged so as to oppose the entire surface of the imaging region 32 on which the pixels 33 are arrayed.

As is known, the pixels 33 includes a photoelectric conversion unit 34 which accumulates the charge (electron-hole pair) by using the incidence of the visible light beams to generate the charge, and a TFT 35 which is a switching element. The photoelectric conversion unit 34 has a structure where a semiconductor layer (for example, PIN type) for generating the charge is arranged between an upper electrode and a lower electrode which are vertically arranged. In the photoelectric conversion unit 34, the TFT 35 is connected to the lower electrode and a bias line is connected to the upper electrode. The bias line is disposed corresponding to the number of the rows of the pixel 33 (corresponding to the n number of rows), and the bias wires are connected to one bus line. The bus line is connected to a bias power source. A bias voltage is applied from the bias power source to the upper electrode of the photoelectric conversion unit 34 through the bus line and the bias line which is a child line of the bus line. Applying the bias voltage generates an electric field inside the semiconductor layer. The charge (electron-hole pair) generated inside the semiconductor layer by the photoelectric conversion moves to the upper electrode and the lower electrode, one of which has a positive polarity and the other of which has a negative polarity. Then, the charge is accumulated in the photoelectric conversion unit 34.

In the TFT 35, a gate electrode is connected to a scanning line 36, a source electrode is connected to a signal line 37 and a drain electrode is connected to the photoelectric conversion unit 34, respectively. The scanning line 36 and the signal line 37 are wired in a latticed pattern. One common scanning line 36 is disposed for each one row of the pixels 33, and is disposed corresponding to the number of rows of the pixels 33 (corresponding to the n number of rows). In addition, one common signal line 37 is disposed for each one column of the pixels 33, and is disposed corresponding to the number of columns of the pixels 33 (corresponding to the m number of columns). The scanning line 36 is connected to a gate driver 38 and the signal line 37 is connected to a signal processing circuit 39.

The circuit portion 31 has the gate driver 38, the signal processing circuit 39 and a control unit 40. By driving the TFT 35 under the control of the control unit 40, the gate driver 38 causes the image detection unit 10 to perform an accumulation operation for accumulating signal charge corresponding to the irradiation dose of X-rays in the pixels 33, a reading-out operation for reading out the accumulated signal charge from the pixels 33, and a reset operation for clearing unnecessary charge accumulated in the pixels 33. In the accumulation operation, the TFT 35 is in a switched-off state, and during the state, the signal charge is accumulated in the pixels 33. In the reading-out operation, gate pulses G1 to Gn which simultaneously drive the TFTs 35 in the same row are sequentially generated from the gate driver 38 at predetermined intervals. Then, the scanning lines 36 are sequentially activated one row by one row, and the TFTs 35 connected to the scanning lines 36 are in a switched-on state one row by one row. The charge accumulated in the photoelectric conversion unit 34 of the pixels 33 is read-out by the signal line 37 in which the TFT 35 is in the switched-on state, and is input to the signal processing circuit 39.

The signal processing circuit 39 includes an integrating amplifier, a CDS circuit, a multiplexer and an A/D converter. The integrating amplifier and the CDS circuit are individually connected to each of the signal lines 37. The integrating amplifier integrates the charge input from the signal lines 37, converts the integrated charge into an analog voltage signal, and output the analog voltage signal. The CDS circuit performs correlated double sampling on the voltage signal output from the integrating amplifier, and holds the voltage signal output from the integrating amplifier for a predetermined time period. The multiplexer uses an electronic switch to select one CDS sequentially from each column of the CDSs connected in parallel with each other, and serially inputs the voltage signal output from the selected CDS to the A/D converter. The A/D converter converts the analog voltage signal input from the multiplexer into a digital pixel value, and outputs the digital pixel value to a memory 41. The pixel value is recorded on the memory 41 by being associated with coordinates of the respective pixels 33.

Each time the gate pulse is generated from the gate driver 38 and the TFTs 35 are in the switched-on state one row by one row, the pixel value of the pixels 33 for one row is recorded in the memory 41. If the entire rows are completely read-out, image data for displaying one sheet of the X-ray image is recorded in the memory 41. After the image data is read-out from the memory 41 and the control unit 40 performs various image processes, the image data is output to an external device such as a console through a communication unit 42. In this manner, the X-ray image of a patient is detected.

The communication unit 42 has an antenna and an oscillation circuit which generate a radio wave for radio communication, and a socket for wired communication, and can correspond to both of the radio communication and the wired communication. The communication unit 42 can communicate information of photographing conditions such as the X-ray image and an X-ray irradiation time period with the external device such as the console. The radio communication may employ optical communication using infrared rays without being limited to the radio wave.

A power supply circuit 43 is connected to the battery unit 15 via the socket 18 of the battery mounting unit 16. Under the control of the control unit 40, the power supply circuit 43 converts power having a predetermined voltage which is supplied from the battery unit 15 into power having a voltage suitable for each unit of the image detection units 10, and supplies the power to each unit. In addition, the power supply circuit 43 monitors a voltage level of the power supplied from the battery unit 15, detects the remaining amount of the battery unit 15 and outputs the detected result to the control unit 40. The control unit 40 switches display of the indicator 24 according to the remaining amount of the battery unit 15 which is sent from the power supply circuit 43. Although not illustrated, a power supply cable extended from an external power source can be connected to the power supply circuit 43, and the power can be received from other power sources except for the battery unit 15.

In FIG. 4, the panel portion 30 and a base 52 to which the circuit portion 31 is attached are arranged inside the housing 11 sequentially from the front surface 12 side. In the present embodiment, the TFT substrate 50 and the scintillator 51 which configure the panel portion 30 adopt an irradiation side sampling (ISS) method in which the TFT substrate 50 and the scintillator 51 are sequentially stacked and arranged when viewed from the front surface 12 side on which the X-ray is incident. The TFT substrate 50 is attached to a rear surface of the transmission plate 13. In this case, the TFT substrate 50 is caused to face the rear surface 14 side so that the imaging region 32 opposes the scintillator 51, and the X-ray transmitting the transmission plate 13 is irradiated from the opposite surface to the surface having the imaging region 32. On the other hand, a penetration side sampling (PSS) method may be adopted in which the scintillator 51 and the TFT substrate 50 are sequentially stacked and arranged. In addition, without using the scintillator 51, a direct conversion type panel portion using a conversion layer (amorphous selenium or the like) which directly converts the X-ray into the charge may be adopted.

The base 52 has a table shape having multiple legs 53. The leg 53 is fixed onto an inner wall surface of the rear surface 14. The base 52 is the largest member whose planar size is largest when viewed from the front surface 12 side out of the members accommodated inside the housing 11. A circuit board 54 is attached to a space on the rear surface 14 side formed by the legs 53 of the base 52. Multiple circuit components 55 configuring the circuit portion 31 are mounted on the circuit board 54. The circuit board 54 is electrically connected to the TFT substrate 50 by a flexible cable 56 which is drawn out by penetrating the base 52.

The housing 11 is configured to have a front surface cover 60 and a rear surface cover 61. The front surface cover 60 and the rear surface cover 61 have a C-shaped cross-section in which four outer peripheral sides of a rectangular flat plate are bent at right angles. Bent portions in the outer periphery of the front surface cover 60 and the rear surface cover 61 configure the side surfaces 19 to 22, and the other portions configure the front surface 12 and the rear surface 14. The front surface cover 60 and the rear surface cover 61 are integrated in such a manner that the front surface cover 60 covers the rear surface cover 61 in a lid shape so as to surround the rear surface cover 61 whose size is slightly smaller than the size of the front surface cover 60.

The front surface cover 60 is a frame body in which a rectangular opening is formed to attach the transmission plate 13 as described above. A groove 62 to which the transmission plate 13 is fitted is formed in the opening of the front surface cover 60. The groove 62 is formed at a position recessed by one step from the surface of the front surface cover 60. Therefore, a step is formed between the surface of the transmission plate 13 and the surface of the front surface cover 60. In order to fill the step up, a protection film 63 made of a resin for transmitting the X-ray is bonded to the surface of the transmission plate 13. This allows the front surface 12 to be a flat surface.

As illustrated in detail in FIG. 5, a chamfered portion 70 configured to have a surface tilted to the side surfaces 21 and 22 and the rear surface 14 is formed between the side surfaces 21 and 22 and the rear surface 14 which correspond to joints of the front surface cover 60 and the rear surface cover 61. In addition, similar to the chamfered portion 70, a chamfered portion 71 is formed between the side surfaces 21 and 22 and the front surface 12. These chamfered portions 70 and 71 allow the front surface 12, the side surfaces 21 and 22, and the rear surface 14 to be connected to each other by a smoothly curved surface having no corner. Therefore, the patient's contact feeling becomes softer. Although not illustrated, the chamfered portions 70 and 71 are also similarly formed between the side surfaces 19 and 20 and the rear surface 14, and between the side surfaces 19 and 20 and the front surface 12. In the following description, the chamfered portion 70 of the illustrated side surface will be described as an example. However, the following description is also similar to the chamfered portion 70 of the side surface (not illustrated).

A shock absorber 72 for protecting the image detection unit 10 against drop impact is embedded inside a portion between the side surfaces 21 and 22 and the front surface 12, in which the chamfered portion 71 of the front surface cover 60 is formed. The shock absorber 72 is formed in a circle whose planar shape surrounds the entire housing 11 when viewed from the front surface 12 side. The shock absorber 72 may be attached not only to the interior of the front surface cover, but also to four outer surface corners of the housing 11 in which the side surfaces 19 to 22 intersect one another.

Figure 6:
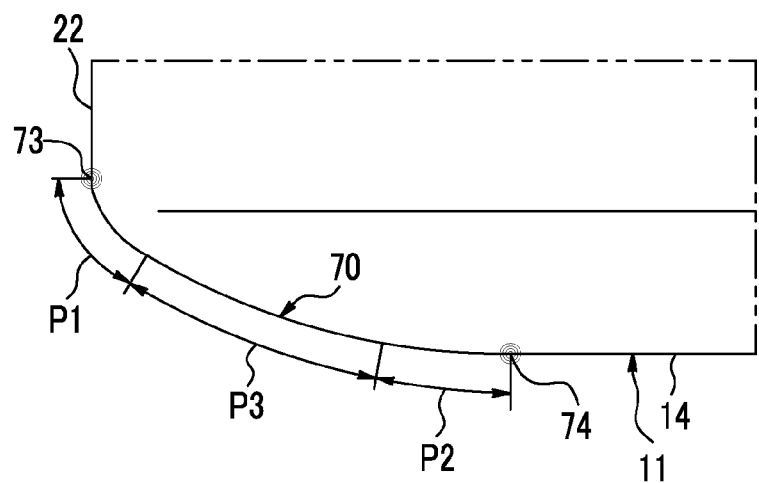
FIG. 6 is an explanatory view of each portion of a chamfered portion.

As illustrated in FIG. 6, the chamfered portion 70 has a boundary portion P1 having a predetermined range in the vicinity of a boundary 73 including the boundary 73 with the side surface 22; a boundary portion P2 having a predetermined range in the vicinity of a boundary 74 including the boundary 74 with the rear surface 14; and the other portion P3 which does not belong to these boundary portions P1 and P2. In order to smoothly insert the chamfered portion 70 into the gap between the patient and the installation surface on which the patient lies on one's back, the entire surface of these boundary portions P1 to P3 is formed in a curved surface which protrudes outward from the housing 11.

In FIG. 5, the chamfered portion 70 satisfies Conditional Expression (1) as below, when assuming that a height of the housing 11 in a thickness direction between the boundaries 73 and 74 (length of a perpendicular line drawn to a surface to which the rear surface 14 is extended from the boundary 73) is h and a length in a horizontal direction which is orthogonal to the thickness direction of the housing 11 between the boundaries 73 and 74 (length of a perpendicular line drawn to a surface to which the side surface 22 is extended from the boundary 74) is d1.

$$h < d1 \qquad \text{Conditional Expression (1)}$$

The base 52 is arranged to satisfy Conditional Expression (2) as below, when assuming that the shortest distance between an end portion 80 of the base 52 and an inner wall surface 81 of the side surface 22 (inner wall surface of a bent side of the rear surface cover 61 which configures the side surface 22) is d2 and the shortest distance between the end portion 80 of the base 52 and an inner wall surface 82 of the chamfered portion 70 is d3.

$$d2 < d3 \qquad \text{Conditional Expression (2)}$$

In other words, the base 52 is arranged so that the space with the chamfered portion 70 is larger than the space with the side surface 22. In addition, when the base 52 is arranged in the thickness direction inside the housing 11, the base 52 is fitted within a range of the height from the boundary 73 to the front surface 12.

The reason why the base 52 is arranged in this manner is to reduce a possibility that when the end portion of the side surface 22 side is inserted into the gap between the patient and the installation surface on which the patient lies on one's back, the patient's weight applied to the end portion may cause the chamfered portion 70 to be recessed inward, the end portion 80 may be brought into contact with the inner wall surface 82, and the influence may damage to the members inside the housing 11.

When the battery mounting unit 16 is arranged in the thickness direction inside the housing 11, the battery mounting unit 16 is fitted within the range of the height from the rear surface 14 to the boundary 73. In other words, the height from the rear surface 14 of the inner wall surface of the battery mounting unit 16 is lower than the height h of the chamfered portion 70. In this manner, when being arranged in the thickness direction inside the housing 11, the battery mounting unit 16 and the base 52 are respectively and separately arranged so that the battery mounting unit 16 is arranged inside the chamfered portion 70 and the base 52 is arranged outside the chamfered portion 70.

Figure 7:
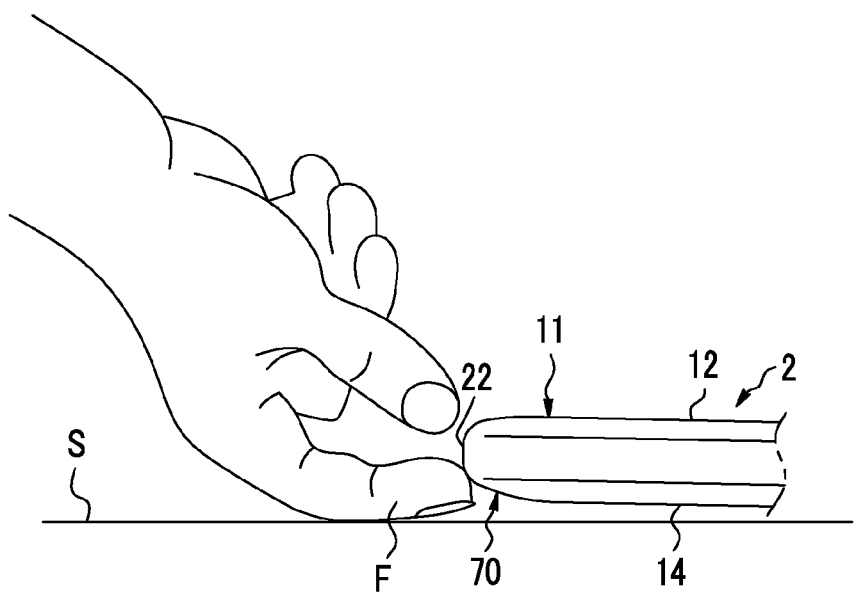
FIG. 7 is a view illustrating a finger's hooked state when an electronic cassette placed on a flat installation surface is lifted up.

Next, an operation according to the above-described embodiment will be described. First, when lifting up the electronic cassette 2 placed on a flat installation surface S such as a floor surface, as illustrated in FIG. 7, a finger F is inserted into the gap formed between the rear surface 14 and the installation surface S by the presence of the chamfered portion 70. Then, the end portion of the side surface 22 side of the housing 11 is raised, thereby using the opportunity to lift the entire housing 11.

Figure 8:
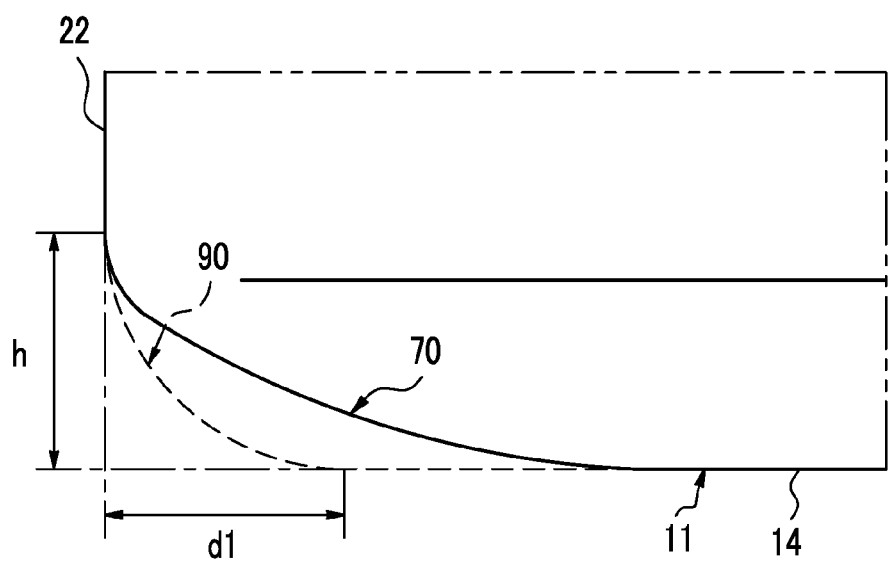
FIG. 8 is a view for comparing chamfered portions in which heights h are the same as each other and the height h of one chamfered portion is equal to a length d1.
Figure 9:
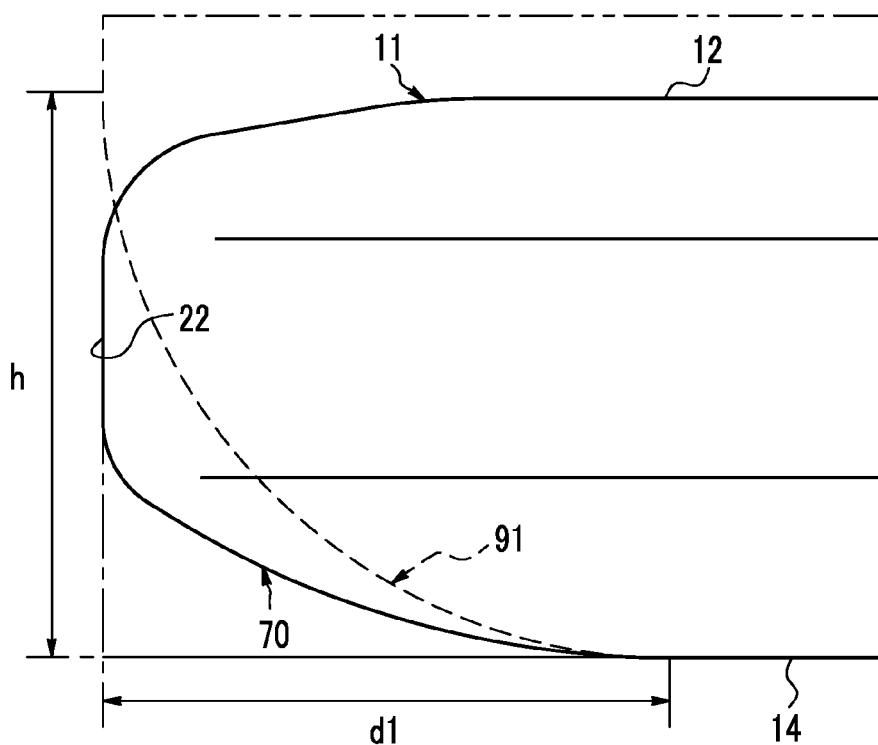
FIG. 9 is a view for comparing chamfered portions in which lengths d1 are the same as each other and the height h of one chamfered portion is equal to the length d1.

The height h and the length d1 of the chamfered portion 70 satisfy Conditional Expression (1). Accordingly, for example, as compared to a chamfered portion 90 illustrated by a dotted line in FIG. 8, in which the height h is the same as that of the chamfered portion 70 and the height is equal to the length d1 (h=d1), the gap between the rear surface 14 and the installation surface S is wide open. Therefore, as compared to a case of h≥d1, the finger F can be further deeply inserted into the gap between the rear surface 14 and the installation surface S, and thus the housing 11 is likely to be raised from the installation surface S. In addition, for example, in a chamfered portion 91 illustrated by a dotted line in FIG. 9, in which the length d1 is the same as that of the chamfered portion 70 and the height is equal to the length d1 (h=d1), the thickness of the housing 11 eventually becomes thicker by an increased amount of the height h. However, in the chamfered portion 70 which satisfies Conditional Expression (1), the thickness of the housing 11 can be thinned. Furthermore, as illustrated in FIG. 10, if the thickness of the housing 11 is adapted to have the same thickness in the example of FIG. 9, the chamfered portion 70 protrudes further outward than the chamfered portion 91. Accordingly, it is possible to widen the internal space of the housing 11. Therefore, it is easy to arrange the base 52 so as to satisfy Conditional Expression (2).

Figure 11A:
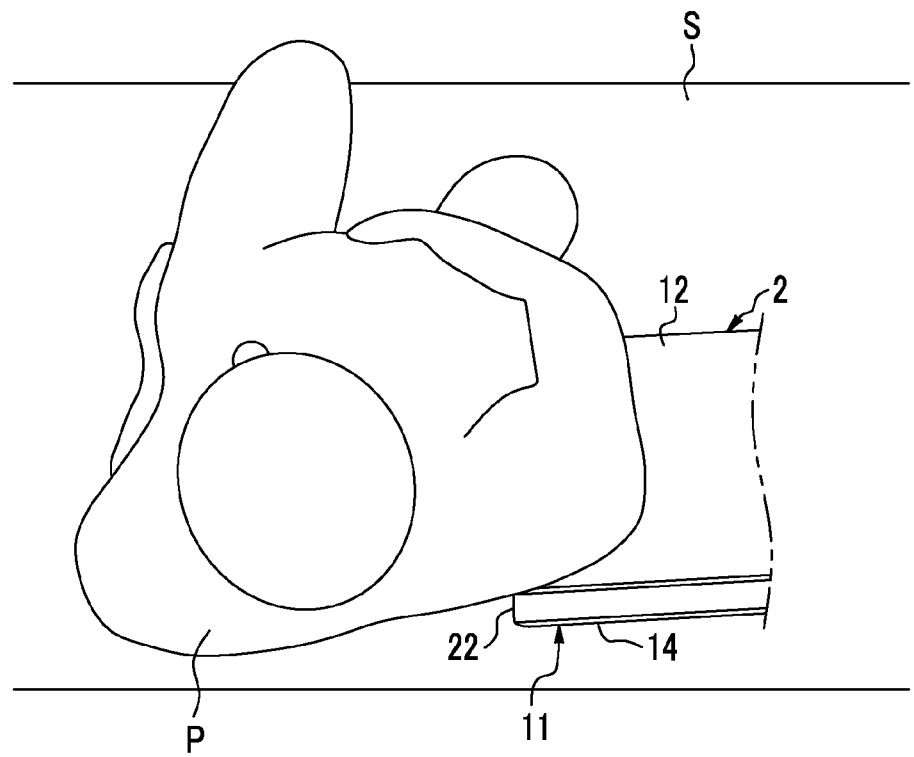
FIGS. 11A and 11b are views illustrating a state when an electronic cassette is inserted into a gap between a patient and an installation surface on which the patient lies on one's back.
Figure 11B:
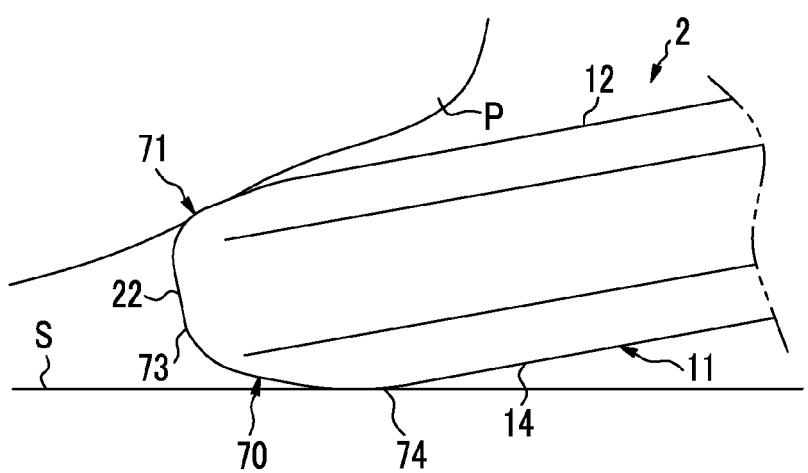

Next, when photographing a patient who cannot move on one's own, such as a patient who lies on one's back on a bed, an aged person or an emergency patient, as illustrated in FIGS. 11A and 11b, in a posture where the electronic cassette 2 is tilted so that one side surface (side surface 22 in the present embodiment) of the housing 11 faces downward, an end portion of the side surface 22 side of the housing 11 is inserted into a gap between a patient P and the installation surface S on which the patient P lies on one's back. Then, while the patient P is lifted up, the housing 11 is further deeply pushed into the gap. In this manner, the electronic cassette 2 is set to be located at a desired photographing position.

When inserting the end portion of the side surface 22 side into the gap between the patient P and the installation surface S, the chamfered portion 70 comes into contact with the installation surface S as illustrated in FIG. 11B. However, the chamfered portion 70 is configured so that the entire surface is formed in a curved surface which protrudes outward from the housing 11 and has no corner to be caught on the installation surface S. Accordingly, the end portion is smoothly inserted into the gap between the patient P and the installation surface S without any resistance. In addition, the chamfered portion 71 is formed between the side surface 22 and the front surface 12 which come into contact with the patient P. Therefore, the patient P has softer contact feeling and thus pain felt by the patient P due to the contact is relieved.

Furthermore, the protection film 63 is bonded to the transmission plate 13 to allow the front surface 12 to be a flat surface. Accordingly, without causing the patient P to feel the pain, it is possible to perform an operation for deeply pushing the housing 11 into the gap. Even when the electronic cassette 2 is removed from the gap between the patient P and the installation surface S after the photographing is completed, the front surface 12 has no concave portion to be caught on clothes of the patient P. Therefore, without causing the patient P to feel pain, it is also possible to smoothly perform the removing operation.

In addition, if the boundary 74 has a corner, the weight of the patient P is intensively put on the corner when the end portion of the housing 11 is inserted into the gap between the patient P and the installation surface S. However, the chamfered portion 70 is configured so that the entire surface is formed in the curved surface which protrudes outward from the housing 11. Accordingly, the weight of the patient is unlikely to be intensively put on one location and correspondingly the housing 11 is unbreakable. Since the corner is not caught on the installation surface S, insertion workability is significantly improved when inserting the end portion of the housing 11 into the gap between the patient P and the installation surface S. Since the weight of the patient P is put on the end portion of the housing 11 during the insertion, if the boundary 74 has the corner, there is resistance to the installation surface S. In contrast, since the chamfered portion 70 is formed in the curved surface which protrudes outward from the housing 11, there is no more possibility of being caught on the installation surface S. Therefore, pushing force to be applied to the housing 11 can be sufficiently reduced during the insertion.

The base 52 is arranged so as to satisfy Conditional Expression (2) and a clearance is formed between the base 52 and the inner wall surface 82 of the chamfered portion 70. Accordingly, when the end portion of the housing 11 is inserted into the gap between the patient P and the installation surface S, there is a decreased possibility that the weight of the patient P which is applied to the end portion may cause the chamfered portion 70 to be recessed inward, the end portion 80 may be brought into contact with the inner wall surface 82, and the influence may damage to the members inside the housing 11. In addition, even if the chamfered portion 70 is recessed inward and the end portion 80 is brought into contact with the inner wall surface 82, the base 52 having the largest planar size serves as a shield to safely protect the TFT substrate 50 and the scintillator 51. In particular, the TFT substrate 50 made of glass is fragile among the members configuring the image detection unit 10. Therefore, if the possibility of damage to the members inside the housing 11 is eliminated in this manner, it is possible to reliably protect the TFT substrate 50.

When the battery mounting unit 16 is arranged in the thickness direction inside the housing 11, the base 52 is fitted within the height from the boundary 73 to the front surface 12 and the battery mounting unit 16 is fitted within the range of the height from the rear surface 14 to the boundary 73. Accordingly, the space from the boundary 73 to the front surface 12 is narrowed by the battery mounting unit 16, and the TFT substrate 50, the scintillator 51 and the base 52 are tightly arranged. Therefore, it is possible to prevent the TFT substrate 50 from being easily damaged when the electronic cassette 2 is dropped by mistake.

The height h and the length d1 of the chamfered portion 70 are preferably higher and longer when considering finger's easy insertion. However, from a viewpoint that the wider internal space of the housing 11 is needed so as to ensure the clearance for withstanding drop impact, the height h and the length d1 are preferably lower and shorter. When considering this counterbalance, it is preferable that the height h of the chamfered portion 70 be 7 mm to 10 mm and the length d1 be 20 mm to 40 mm. If the height of the chamfered portion 70 is lower than 7 mm, the gap for allowing the finger F to be inserted is not sufficiently open and thus it is difficult to raise the housing 11 from the installation surface S. Similarly, when the length d1 is shorter than 20 mm, the finger F is not deeply pushed into the gap. In addition, if the height h is higher than 10 mm, the internal space of the housing 11 is compressed correspondingly. The same applies to a case where the length d1 of the chamfered portion 70 is longer than 40 mm. If the internal space of the housing 11 is narrowed, a distance d3 between the end portion 80 of the base 52 and the inner wall surface 82 of the chamfered portion 70 is also shortened. Accordingly, in order to satisfy Conditional Expression (2), it is necessary to increase the height of the legs 53 so as to further separate the end portion 80 of the base 52 from the inner wall surface 82 of the chamfered portion 70. Therefore, the thickness of the housing 11 becomes thicker correspondingly.

Figure 12A:
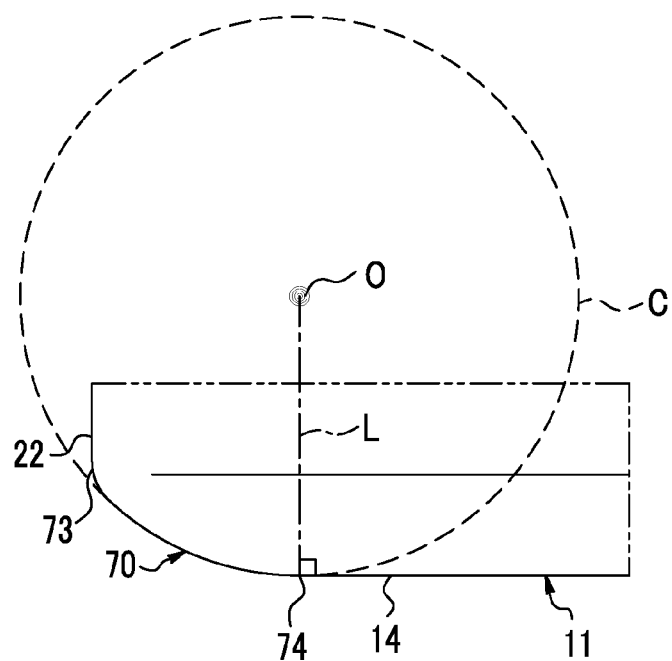
FIGS. 12A and 12B are explanatory views of a shape of a chamfered portion.
Figure 12B:
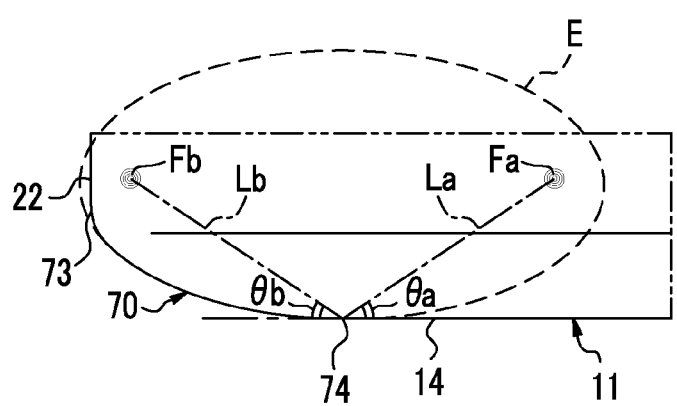

As a more specific shape of the chamfered portion 70, as illustrated in FIG. 12A, it is preferable that a cross-sectional shape when viewed from the side surface 19 side be an arc which is formed by cutting off a portion from a perfect circle C. The rear surface 14 intersects a line L extended from a center O of the perfect circle C to the boundary 74 at right angles. That is, the rear surface 14 is a tangent to the perfect circle C, and the boundary 74 is a tangent point to the perfect circle C. In addition, as illustrated in FIG. 12B, the chamfered portion 70 may adopt an elliptical arc which is formed by cutting off a portion from an ellipse E. In this case, an angle $\theta a$ formed between a straight line La connecting a focal point Fa of the ellipse E to the boundary 74 and the rear surface 14 is equal to an angle $\theta b$ formed between a straight line Lb connecting another focal point Fb of the ellipse E to the boundary 74 and an extended surface of the rear surface 14 ($\theta a = \theta b$)). That is, even in this case, the rear surface 14 is a tangent to the ellipse E and the boundary 74 is a tangent point to the ellipse E.

Only the boundary portion P1 having a predetermined range in the vicinity of the boundary 73 is formed in a curved surface which is different from the arc or the elliptical arc which is formed by cutting off a portion from the perfect circle C or the ellipse E. As can be understood from this configuration, the chamfered portion 70 may be formed so as not to have corners by connecting multiple arcs or elliptical arcs which are formed by cutting off portions from multiple perfect circles or ellipses.

In the above-described embodiment, the chamfered portion 70 in which the entire surface is formed in the curved surface which protrudes outward from the housing 11 has been described as an example. However, the present invention is not limited thereto. For example, the present invention may adopt a chamfered portion in which the boundary portion P1 excluding the boundary 73, and the boundary portions P2 and P3 are formed in a curved surface which protrudes outward from the housing 11 and the boundary 73 has a corner.

Figure 13A:
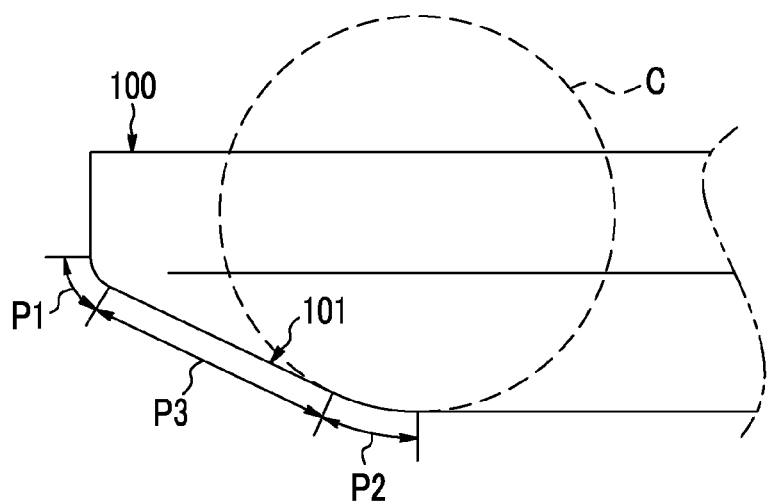
FIGS. 13A and 13B are views illustrating other examples of a chamfered portion.

Alternatively, as in a housing 100 illustrated in FIG. 13A, the present invention may adopt a chamfered portion 101 in which only the boundary portions P1 and P2 are formed in a curved surface which protrudes outward from the housing 11 and the other boundary portion P3 is formed in a planar shape. In addition, as in a housing 105 illustrated in FIG. 13B, the present invention may adopt a chamfered portion 106 in which only the boundary portion P2 is formed in a curved surface which protrudes outward from the housing 11 and the other boundary portions P1 and P3 are formed in a planar shape. In short, at least the boundary portion P2 may be formed in a curved surface which protrudes outward from the housing 11. Therefore, the chamfered portion 71 according to the above-described embodiment may not be formed.

As illustrated in FIGS. 11A and 11B, when photographing a patient who cannot move on one's own, such as a patient who lies on one's back on a bed, an aged person or an emergency patient, in a posture where the electronic cassette 2 is tilted so that one side surface of the housing 11 faces downward, the end portion of the side surface 22 side of the housing 11 is inserted into the gap between the patient and the installation surface. Accordingly, the chamfered portion 101 illustrated in FIG. 13A or the chamfered portion 106 illustrated in FIG. 13B first comes into contact with the installation surface. However, while this contact state is changed to a state where the housing 11 is inserted into a portion under the patient and the rear surface 14 is completely in contact with the installation surface, the housing 11 is not caught on the installation surface since at least the boundary portion P2 is formed in the curved surface which protrudes outward from the housing 11. Depending on shapes of the boundary portion P2, there is a small difference. However, depending on whether or not the boundary portion P2 has a corner, the boundary portion P2 greatly contributes to significantly improved insertion workability when inserting the boundary portion P2 into the gap between the patient and the installation surface.

Figure 13B:
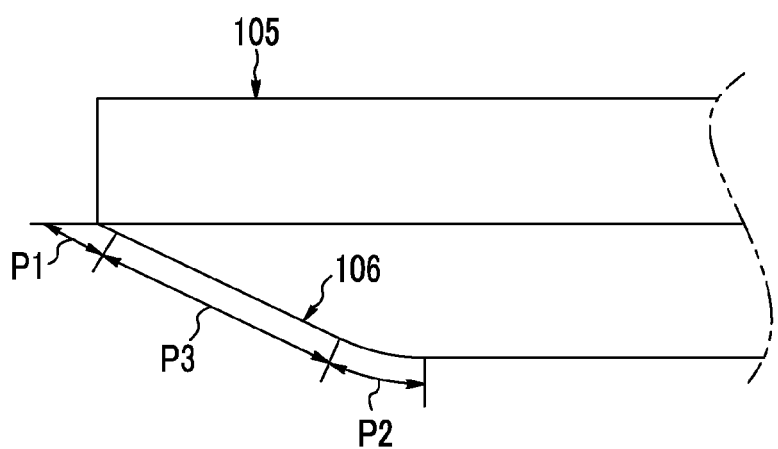

When adopting the examples illustrated in FIGS. 13A and 13B, as compared to the chamfered portion 70, a planar portion has a shape in which the housing is cut off further inward. Accordingly, it is easy to push the finger deeply into the gap. In addition, when inserting the end portion of the housing into the gap between the patient and the installation surface, the planar portion comes into surface contact with the installation surface. Accordingly, as compared to the chamfered portion 70 in the above-described embodiment, the contact area with the installation surface is increased and the resistance is increased correspondingly. However, as compared to the chamfered portion 70, the chamfered portions receive the dispersed weight of the patient and thus are unlikely to be recessed inward. However, as compared to a case where the entire surface of the chamfered portion is formed in the curved surface which protrudes outward from the housing, the internal space of the housing is compressed and it is difficult to form a clearance for buffering the impact between the base and the inner wall surface of the chamfered portion. Therefore, it is preferable that the entire surface of the chamfered portion be formed in the curved surface which protrudes outward from the housing 11 as in the above-described embodiment.

Even in a case of the chamfered portion including the above-described plane, a portion formed in the curved surface which protrudes outward from the housing 11 may be configured to be an arc which is formed by cutting off a portion from the perfect circle C as illustrated by a dotted line in FIG. 13A, the rear surface may be the tangent to the perfect circle C, and the boundary between the chamfered portion and the rear surface may be the tangent point. Alternatively, although not illustrated, the portion may be configured to be an elliptical arc which is formed by cutting off a portion from an ellipse, the rear surface may be the tangent to the ellipse, and the boundary between the chamfered portion and the rear surface may be the tangent point.

In the above-described embodiment, the chamfered portion is disposed between all of four side surfaces and the rear surface. However, the chamfered portion may be disposed between at least one side surface and the rear surface.

In the above-described embodiment, a portion of the housing is configured to be the chamfered portion and the chamfered portion is disposed integrally with the housing. However, the housing and the chamfered portion may be separate members from each other, and the electronic cassette may be configured by assembling the separate members with each other.

In the above-described embodiment, the base has been described as an example of the largest member whose planar size is largest among the members accommodated inside the housing, but the present invention is not limited thereto. For example, when the base is not required by disposing legs similar to the base in a circuit board, the circuit board can be the largest member.

In the above-described embodiment, the image detection unit of the TFT type has been described as an example. However, the present invention may adopt an image detection unit of a complementary metal oxide semiconductor (CMOS) type. Furthermore, without being limited to the X-ray, the present invention can also be applied to a case where other radiation rays such as γ-rays are used in radiography.

What is claimed is:

1. An electronic cassette comprising:
   an image detection unit that detects a radiographic image of a photographic subject;
   a rectangular parallelepiped housing that accommodates the image detection unit, and that has a front surface on which radiation is incident, a rear surface opposing the front surface, and four side surfaces; and
   a chamfered portion that is disposed between at least one of the side surfaces and the rear surface, and that is configured to have a surface tilted to the side surface and the rear surface,
   wherein a boundary portion between the chamfered portion and the rear surface is formed in a curved surface which protrudes outward from the housing,
   wherein the chamfered portion satisfies a condition of h<d1 when assuming that a height of the housing in a thickness direction is h and a length in a horizontal direction which is orthogonal to the thickness direction is d1 in the respective boundaries between the rear surface and the side surface, and
   wherein the height h is 7 mm to 10 mm and the length d1 is 20 mm to 40 mm.

2. The electronic cassette according to claim 1
   wherein in a cross-sectional shape of the chamfered portion, the boundary portion with the rear surface is an arc or an elliptical arc which is formed by cutting off a portion from a perfect circle or an ellipse.

3. The electronic cassette according to claim 2,
   wherein the rear surface is a tangent to the perfect circle or the ellipse, and a boundary between the chamfered portion and the rear surface is a tangent point to the perfect circle or the ellipse.

4. The electronic cassette according to claim 1,
   wherein the largest member out of members accommodated inside the housing satisfies a condition of d2<d3 when assuming that the shortest distance between an end portion of the largest member whose planar size is largest and an inner wall surface of the side surface is d2 and the shortest distance between the end portion of the largest member and an inner wall surface of the chamfered portion is d3.

5. The electronic cassette according to claim 4,
   wherein the largest member is a base to which a circuit board is attached.

6. The electronic cassette according to claim 4,
   wherein when the largest member is arranged in the thickness direction inside the housing, the largest member is fitted within a range of a height from a boundary between the chamfered portion and the side surface to the front surface.

7. The electronic cassette according to claim 6,
   wherein the rear surface has a battery mounting unit on which a battery unit for supplying power to the image detection unit is detachably mounted and which is a concave portion in which the rear surface is recessed toward the front surface, and
   wherein when the battery mounting unit is arranged in the thickness direction inside the housing, the battery mounting unit is fitted within a range of a height from the rear surface to the boundary between the chamfered portion and the side surface.

8. An electronic cassette comprising:
   an image detection unit that detects a radiographic image of a photographic subject;
   a rectangular parallelepiped housing that accommodates the image detection unit, and that has a front surface on which radiation is incident, a rear surface opposing the front surface, and four side surfaces; and
   a chamfered portion that is disposed between at least one of the side surfaces and the rear surface, and that is configured to have a surface tilted to the side surface and the rear surface,
   wherein a boundary portion between the chamfered portion and the rear surface is formed in a curved surface which protrudes outward from the housing, and
   wherein the largest member out of members accommodated inside the housing satisfies a condition of d2<d3 when assuming that the shortest distance between an end portion of the largest member whose planar size is largest and an inner wall surface of the side surface is d2 and the shortest distance between the end portion of the largest member and an inner wall surface of the chamfered portion is d3.

9. The electronic cassette according to claim 8,
   wherein when the largest member is arranged in the thickness direction inside the housing, the largest member is fitted within a range of a height from a boundary between the chamfered portion and the side surface to the front surface.

10. An electronic cassette comprising:
    an image detection unit that detects a radiographic image of a photographic subject;
    a rectangular parallelepiped housing that accommodates the image detection unit, and that has a front surface on which radiation is incident, a rear surface opposing the front surface, and four side surfaces; and
    a chamfered portion that is disposed between at least one of the side surfaces and the rear surface, and that is configured to have a surface tilted to the side surface and the rear surface,
    wherein a boundary portion between the chamfered portion and the rear surface is formed in a curved surface which protrudes outward from the housing,
    wherein an entire surface of the chamfered portion which includes a boundary portion with the rear surface and a boundary portion with the side surface is formed in a curved surface which protrudes outward from the housing, and wherein the largest member out of members accommodated inside the housing satisfies a condition of $d2<d3$ when assuming that the shortest distance between an end portion of the largest member whose planar size is largest and an inner wall surface of the side surface is $d2$ and the shortest distance between the end portion of the largest member and an inner wall surface of the chamfered portion is $d3$.

11. The electronic cassette according to claim 10,
wherein when the largest member is arranged in the thickness direction inside the housing, the largest member is fitted within a range of a height from a boundary between the chamfered portion and the side surface to the front surface.

* * * * *